(12) United States Patent
Parrott et al.

(10) Patent No.: US 11,351,207 B2
(45) Date of Patent: Jun. 7, 2022

(54) **USE OF DIRECT-FED MICROBIALS IN PREVENTING AND/OR TREATING *E. COLI*-BASED INFECTIONS IN ANIMALS**

(71) Applicant: DuPont Nutrition Biosciences APS, Copenhagen K (DK)

(72) Inventors: Terry Parrott, El Reno, OK (US); Laura Payling, Manawatu (NZ)

(73) Assignee: DUPONT NUTRITION BIOSCIENCES APS

( * ) Notice: Subject to any disclaimer, the term of this patent is extended or adjusted under 35 U.S.C. 154(b) by 0 days.

(21) Appl. No.: 16/977,514

(22) PCT Filed: Mar. 4, 2019

(86) PCT No.: PCT/US2019/020482
§ 371 (c)(1),
(2) Date: Sep. 2, 2020

(87) PCT Pub. No.: WO2019/173174
PCT Pub. Date: Sep. 12, 2019

(65) Prior Publication Data
US 2021/0000892 A1    Jan. 7, 2021

Related U.S. Application Data

(60) Provisional application No. 62/639,158, filed on Mar. 6, 2018.

(51) Int. Cl.
| | | |
|---|---|---|
| *A01N 63/00* | (2020.01) | |
| *A61K 35/742* | (2015.01) | |
| *A61P 31/04* | (2006.01) | |
| *A61K 9/00* | (2006.01) | |
| *A61K 38/46* | (2006.01) | |
| *A61K 38/47* | (2006.01) | |
| *A61K 38/48* | (2006.01) | |

(52) U.S. Cl.
CPC .......... *A61K 35/742* (2013.01); *A61K 9/0056* (2013.01); *A61K 38/465* (2013.01); *A61K 38/47* (2013.01); *A61K 38/48* (2013.01); *A61P 31/04* (2018.01)

(58) Field of Classification Search
CPC ...... A61K 49/00; A61K 39/00; A61K 35/743; A01N 63/00
USPC ................... 424/9.1, 9.2, 93.1, 93.4, 93.462
See application file for complete search history.

(56) References Cited

U.S. PATENT DOCUMENTS

| | | | |
|---|---|---|---|
| 8,021,654 B2 * | 9/2011 | Rehberger | ............. A23K 50/30 424/93.3 |
| 2005/0255092 A1 | 11/2005 | Rehberger et al. | |
| 2009/0280090 A1 | 12/2009 | Peterson et al. | |
| 2017/0014516 A1 | 1/2017 | Rehberger et al. | |

FOREIGN PATENT DOCUMENTS

| | | |
|---|---|---|
| WO | 2007044968 A2 | 4/2007 |
| WO | 2013329013 A1 | 2/2013 |
| WO | 2017083196 A1 | 5/2017 |

OTHER PUBLICATIONS

Lee et al., Effect of Bacillus-based direct-fed microbials on Eimeria maxima infection in broiler chickens, Comparative mmunology, Microbiology and Infectious Diseases, Pergamon Press, Oxford, vol. 33, No. 6, Dec. 1, 2010, pp. e105-e110.

Lee et al., Bacillus subtilis-based direct-fed microbials augment macrophage function in broiler chickens, Research in Veterinary Science, vol. 91, No. 3, Dec. 1, 2011, pp. e87-e91.

* cited by examiner

*Primary Examiner* — Albert M Navarro

(57) ABSTRACT

A composition and method for preventing and/or treating an *E. coli*-based infection in an animal is described.

10 Claims, 1 Drawing Sheet

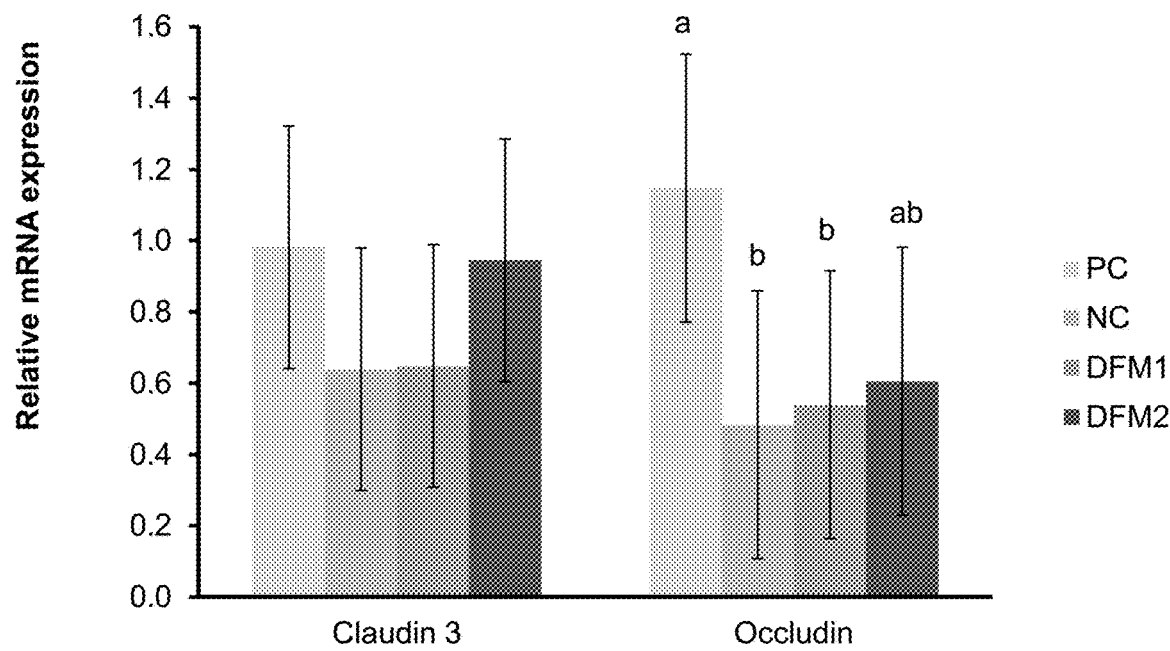
Effect of dietary treatment on expression of tight junction proteins

USE OF DIRECT-FED MICROBIALS IN PREVENTING AND/OR TREATING *E. COLI*-BASED INFECTIONS IN ANIMALS

CROSS-REFERENCE TO RELATED APPLICATIONS

This application is a U.S. national phase entry under 35 U.S.C. § 371 of International Patent Application No. PCT/US2019/020482, filed Mar. 4, 2019 which claims priority to U.S. Provisional Patent Application No. 62/639,158, filed Mar. 6, 2018, the disclosure of each of which is incorporated by reference herein in its entirety.

FIELD

The field relates to the use of direct-fed microbials in preventing and/or treating animals having an *E. coli*-based infection.

BACKGROUND

*Escherichia coli* (*E. coli*) is a gram-negative, rod-shaped bacterium that normally inhabits the intestinal microflora or ecosystem of most mammalian and bird species. *E. coli* is classified into 150 to 200 serotypes or serogroups based on somatic (O), capsular (K), fimbrial (F) and flagellar (H) antigens. Most *E. coli* are commensals, that is, they reside in the intestine but are not harmful for the host animal. Only a small proportion of strains are pathogenic, producing virulence factors permitting them to cause disease. Some *E. coli* possess virulence genes in combinations not known to be associated with disease, and may be considered as potentially pathogenic. All *E. coli* may carry genes for resistance to antimicrobial agents.

In animals, virulent strains of *E. coli* are responsible of a variety of diseases, among others septicemia and diarrhea in newborn calves, acute mastitis in dairy cows, colibacillosis also associated with chronic respiratory disease with *Mycoplasma* where it causes perihepatitis, pericarditis, septicemic lungs, peritonitis etc. in poultry, and Alabama rot in dogs.

*E. coli* bacteria are constantly being shed into the immediate environment of the animals via the faeces, and contaminate the pens, litter, and floor of animals being housed indoors and the soil for outdoor animals. They can persist for long periods, possibly more than 10 weeks, and be spread via slurry and manure to fertilized fields and crops, and to ground and surface water.

*E. coli* is transmitted to other animals via contaminated feed, handlers, and drinking water, and possibly farm to farm by vehicles such as transport trucks. Infection occurs by the oral route or via inhalation of contaminated dust in the case of birds. *E. coli* from animals may also be transmitted to humans by direct contact, or ingestion of food or water contaminated following spread of manure, or ingestion of meat following contamination of carcasses at the slaughterhouse. Intestinal infection due to Enterotoxigenic *Escherichia* (*E.*) *coli* (ETEC) is the most common type of colibacillosis of young animals, such as pigs and calves, typically appearing as severe watery diarrhea. It is also a significant cause of diarrhea among travelers ("Traveler's Diarrhea") and children in the developing world.

ETEC in pigs is often contagious, the same strain being found in high numbers and in several sick pigs and from one batch to another. These strains are usually only shed for a few days after infection, probably due to the development of immunity.

Use of antibiotics in treating both humans and animals has resulted in antimicrobial resistance that now has become a major global health threat. The quest is on for developing alternatives to antibiotics in order to address this global health concern. Thus, there is a need to find new and alternative approaches for preventing and/or treating *E. coli*-based infections in animals.

SUMMARY

In one embodiment, there is disclosed a composition for preventing and/or treating an *E. coli*-based infection in an animal wherein said composition comprises a direct-fed microbial *Bacillus*-based component comprising *Bacillus subtilis* strain 3BP5 (NRRL B-50510); *Bacillus amyloliquefaciens* 918 (NRRL B-50508), and *Bacillus subtilis* subsp. *subtilis* 15A-P4 (PTA-6507).

In a second embodiment, the composition disclosed herein can produce one or more performance benefits in the animal, the performance benefit being selected from the group consisting of increased bodyweight gain, gain feed ratio, improved gut barrier integrity, decreased mortality, and reduced *E. coli* shedding in feces.

In a third embodiment, the direct-fed microbial is in the form of an endospore.

In a fourth embodiment, any of the compositions described herein further comprise at last one enzyme which, optionally, may be encapsulated.

In a fifth embodiment, at least one enzyme is selected from the group consisting of phytase, protease, amylase, xylanase and beta-glucanase.

In a sixth embodiment, any of the compositions described herein can be a feed additive composition or a premix.

In a seventh embodiment, there is disclosed feed comprising any of the feed additive compositions disclosed herein.

In an eighth embodiment, there is disclosed a kit comprising any of the feed additive compositions disclosed herein and instructions for administration.

In a ninth embodiment, there is disclosed a method for preventing and/or treating an *E. coli*-based infection in an animal which comprises administering an effective amount of a composition comprising a direct-fed microbial comprising *Bacillus subtilis* strain 3BP5 (NRRL B-50510); *Bacillus amyloliquefaciens* 918 (NRRL B-50508), and *Bacillus subtilis* subsp. *subtilis* 15A-P4 (PTA-6507). The composition so administered can produce one or more performance benefits in the animal, the performance benefit being selected from the group consisting of increased bodyweight gain, gain feed ratio, improved gut barrier integrity, reduced mortality and reduced *E. coli* shedding in feces. This composition can encompass any of the features described above or elsewhere in this disclosure.

BRIEF DESCRIPTION OF THE DRAWINGS

FIG. 1 shows the effect of dietary treatment on expression of tight junction proteins as an indicator of gut health.

DETAILED DESCRIPTION

All patents, patent applications, and publications cited are incorporated herein by reference in their entirety.

In this disclosure, a number of terms and abbreviations are used. The following definitions apply unless specifically stated otherwise.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The terms "animal" and "subject" are used interchangeably herein. An animal includes all non-ruminant (including humans) and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal can be multigastric, such as a ruminant animal, including, but not limited to, cattle, young calves, goats, sheep, giraffes, bison, moose, elk, yaks, water buffalo, deer, camels, alpacas, llamas, antelope, pronghorn and nilgai.

The term "ruminant" as used herein refers to a mammal that is able to acquire nutrients from plant-based food by fermenting it in a specialized stomach prior to digestion, principally, through microbial actions. The process typically requires the fermented ingesta (known as cud) to be regurgitated and chewed again. The process of rechewing the cud to further break down plant matter and stimulate digestion is called rumination. Roughly 150 species of ruminants include both domestic and wild species. Ruminating animals include, but are not limited to, cattle, cows, goats, sheep, giraffes, yaks, deer, elk, antelope, buffalo and the like.

The term "CFU" as used herein means "colony forming units" and is a measure of viable cells in which a colony represents an aggregate of cells derived from a single progenitor cell. The term "direct-fed microbial" ("DFM") as used herein is source of live (viable) naturally occurring microorganisms. A DFM can comprise one or more of such naturally occurring microorganisms such as bacterial strains. Categories of DFMs include spore-forming bacteria such as *Bacillus* and *Clostridium* as well non-spore forming bacteria such as Lactic Acid Bacteria, Yeasts and Fungi. Thus, the term DFM encompasses one or more of the following: direct fed bacteria, direct fed yeast, direct fed yeast or fungi and combinations thereof.

*Bacillus* is a unique, gram-positive rod that forms spores. These spores are very stable and can withstand environmental conditions such as heat, moisture and a range of pH. These spores germinate into active vegetative cells when ingested by an animal and can be used in meal and pelleted diets.

The term "*Bacillus*-based component" as used herein refers to (i) a *Bacillus*-based direct fed microbial comprising the *Bacillus* bacterial strains described herein, (ii) a supernatant obtained from a *Bacillus* culture made from these strains or (iii) a combination of (i) and (ii).

A "feed" and a "food", respectively, means any natural or artificial diet, meal or the like or components of such meals intended or suitable for being eaten, taken in, digested, by a non-human animal and a human being, respectively.

As used herein, the term "food" is used in a broad sense—and covers food and food products for humans as well as food for non-human animals (i.e. a feed).

The term "feed" is used with reference to products that are fed to animals in the rearing of livestock. The terms "feed" and "animal feed" are used interchangeably. In a preferred embodiment, the food or feed is for consumption by monogastric and multigastric animals.

The term "probiotic" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

The term "prebiotic" means a non-digestible food ingredient that beneficially affects the host by selectively stimulating the growth and/or the activity of one or a limited number of beneficial bacteria.

The term "pathogen" as used herein means any causative agent of disease. Such causative agents can include, but are not limited to, bacterial, viral, fungal causative agents and the like.

The term "*E. coli*-based infection" means a disease or infection, such as diarrhea caused by *E. coli* bacteria.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "effective amount" means a sufficient amount of the specified component administered to an animal to achieve the desired effect.

In one embodiment, there is disclosed a composition for preventing and/or treating an *E. coli*-based infection in an animal wherein said composition comprises a direct-fed microbial *Bacillus*-based component comprising *Bacillus subtilis* strain 3BP5 (NRRL B-50510); *Bacillus amyloliquefaciens* strains 918 (NRRL B-50508), and *Bacillus subtilis* subsp. *subtilis* 15A-P4 (PTA-6507).

In a second embodiment, the composition disclosed herein can produce one or more performance benefits in the animal, the performance benefit being selected from the group consisting of increased bodyweight gain, gain feed ratio, improved gut barrier integrity and reduced *E. coli* shedding in feces.

The *Bacillus*-based DFM component described herein may comprise viable bacteria or may comprise supernatant or be a combination of viable bacteria and culture supernatant. The preferred *Bacillus*-based DFM component is viable bacteria.

In one embodiment, the DFM may be a spore forming bacterial strain and hence the term DFM may be comprised of or contain spores, e.g. bacterial spores. Thus, the term "viable bacteria" as used herein may include bacterial spores, such as endospores or conidia. Alternatively, the DFM in a feed additive composition described herein may not comprise of or may not contain bacterial spores, e.g. endospores or conidia.

The *Bacillus*-based DFM component described herein is a combination of the following strains:

*Bacillus subtilis* strain 3BP5 Accession No. NRRL B-50510,

*Bacillus* amyloliqufaciens strain 918 ATCC Accession No. NRRL B-50508, and

*Bacillus* amyloliqufaciens strain 1013 ATCC Accession No. NRRL B-50509.

Strains 3BP5 and 1013 are described in WO2013-329013 which was published on Feb. 28, 2013.

Strain 15A-P4 is described in US 2005-0255092 which was published on Nov. 17, 2005.

In some embodiments, it is important that the *Bacillus*-based DFM component be heat tolerant, i.e., is thermotolerant e.g., spore-forming. This is particularly the case when feed is pelleted. Bacilli are able to form stable endospores when conditions for growth are unfavorable and are very resistant to heat, pH, moisture and disinfectants. If the bacterium/DFM is not a spore-former then it should be protected to survive feed processing as is described hereinbelow.

A *Bacillus*-based component as described herein may be prepared as culture(s) and carrier(s) (where used) and can be added to a ribbon or paddle mixer and mixed for about 15 minutes, although the timing can be increased or decreased. The components are blended such that a uniform mixture of the cultures and carriers result. The final product is preferably a dry, flowable powder. Accordingly, a *Bacillus*-based component can comprise a: a *Bacillus*-based direct fed microbial comprising the three *Bacillus* bacterial strains described herein or a supernatant obtained from a *Bacillus* culture or a combination of both *Bacillus* bacterial strain or strains and supernatant. Such a *Bacillus*-based component can then be added to animal feed or a feed premix. It can be added to the top of the animal feed ("top feeding") or it can be added to a liquid such as the animal's drinking water.

Inclusion of the individual strains in the *Bacillus*-based DFM as described herein can be in proportions varying from 1% to 99% and, preferably, from 25% to 75%.

Suitable dosages of the *Bacillus*-based component as described herein in animal feed may range from about $1\times10^3$ CFU/g feed to about $1\times10^{10}$ CFU/g feed, suitably between about $1\times10^4$ CFU/g feed to about $1\times10^8$ CFU/g feed, suitably between about $7.5\times10^4$ CFU/g feed to about $1\times10^7$ CFU/g feed.

A person of ordinary skill in the art will readily be aware of specific species and/or strains of microorganisms from within the genera described herein which are used in the food and/or agricultural industries and which are generally considered suitable for animal consumption. Animal feeds may include plant material such as corn, wheat, sorghum, soybean, canola, sunflower or mixtures of any of these plant materials or plant protein sources for poultry, pigs, ruminants, aquaculture and pets.

The terms "animal feed", "feed", and "feedstuff" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

When used as, or in the preparation of, a feed, such as functional feed, a *Bacillus*-based component as described herein may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment, a *Bacillus*-based component as described herein may be admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment the term "feed component" encompasses a premix or premix constituents. Preferably, the feed may be a fodder, or a premix thereof, a compound feed, or a premix thereof. A feed additive composition comprising a *Bacillus*-based component as described herein may be admixed with a compound feed or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes hay, straw, silage, compressed and pelleted feeds, oils and mixed rations, and also sprouted grains and legumes.

Fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff described herein may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

Furthermore, such feedstuff may contain at least 30%, at least 40%, at least 50% or at least 60% by weight corn and soybean meal or corn and full fat soy, or wheat meal or sunflower meal.

In addition, or in the alternative, a feedstuff may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

As described herein, feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

The term feed as used herein also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed may also encompass in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

Also encompassed within the term "feed" is bird food including food that is used both in birdfeeders and to feed pet birds. Typically, bird food comprises of a variety of seeds, but may also encompass suet (beef or mutton fat).

As used herein the term "contacted" refers to the indirect or direct application of the feed additive composition to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

The *Bacillus*-based component may be preferably admixed with the product (e.g. feedstuff). Alternatively, it may be included in the emulsion or raw ingredients of a feedstuff.

For some applications, it is important that it is made available on or to the surface of a product to be affected/treated.

The *Bacillus*-based component may be applied to intersperse, coat and/or impregnate a product (e.g. feedstuff or raw ingredients of a feedstuff) with a controlled amount of a *Bacillus*-based component.

The DFMs described herein can be added in suitable concentrations, for example, in concentrations in the final feed product which offer a daily dose of between about $2 \times 10^3$ CFU/g of feed to about $2 \times 10^{11}$ CFU/g of feed, suitably between about $2 \times 10^6$ to about $1 \times 10^{10}$, suitably between about $3.75 \times 10^7$ CFU/g of feed to about $1 \times 10^{10}$ CFU/g of feed.

Preferably, the *Bacillus*-based component will be thermally stable to heat treatment up to about 70° C.; up to about 85° C.; or up to about 95° C. The heat treatment may be performed from about 30 seconds up to several minutes. The term "thermally stable" means that at least about 50% of *Bacillus*-based component that was present/active before heating to the specified temperature are still present/active after it cools to room temperature. In a particularly preferred embodiment the *Bacillus*-based component is homogenized to produce a powder.

Alternatively, the *Bacillus*-based component is formulated to granules as described in WO2007/044968 (referred to as TPT granules) incorporated herein by reference.

In another preferred embodiment when the feed additive composition is formulated into granules, the granules comprise a hydrated barrier salt coated over the protein core. The advantage of such salt coating is improved thermo-tolerance, improved storage stability and protection against other feed additives otherwise having adverse effect on the at least one protease and/or DFM comprising one or more bacterial strains. Preferably, the salt used for the salt coating has a water activity greater than 0.25 or constant humidity greater than 60% at 20° C. Preferably, the salt coating comprises a $Na_2SO_4$.

Feed containing the *Bacillus*-based component may be produced using a feed pelleting process. Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The *Bacillus*-based component may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

A granule may be produced using a steam-heated pelleting process which may be conducted between 85° C. and 95° C. for up to several minutes.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the *Bacillus*-based component onto a carrier substrate, such as ground wheat for example.

In one embodiment, such feed additive composition comprising a *Bacillus*-based component as described herein may be formulated as a premix. By way of example only the premix may comprise one or more feed components, such as one or more minerals and/or one or more vitamins.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g., spraying, the *Bacillus*-based component onto a carrier substrate, such as ground wheat for example.

In one embodiment such *Bacillus*-based component as described herein may be formulated as a premix. By way of example only the premix may comprise one or more feed components, such as one or more minerals and/or one or more vitamins.

It will be understood that *Bacillus*-based component as disclosed herein is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins. Preferably, the feedstuff is a corn soybean meal mix.

In another aspect, there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular, by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

The *Bacillus*-based component described herein may be placed on top of the animal feed, i.e., top fed. Alternatively, the *Bacillus*-based component described herein may be added to a liquid such as in the drinking water of the animal.

As used herein the term "contacted" refers to the indirect or direct application of a *Bacillus*-based component as described herein to a product (e.g. the feed).

Examples of application methods which may be used, include, but are not limited to, treating the product in a material comprising the *Bacillus*-based component, direct application by mixing a feed additive composition *Bacillus*-based component as described herein with the product, spraying such feed additive composition onto the product surface or dipping the product into a preparation of the feed additive composition. In one embodiment a feed additive composition *Bacillus*-based component as described herein is preferably admixed with the product (e.g. feedstuff).

Alternatively, the feed additive composition may be included in the emulsion or raw ingredients of a feedstuff. This allows the composition to impart a performance benefit.

A method of preparing the *Bacillus*-based component as described herein may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minute, 2 minutes, 5 minutes, 10 minutes, 15 minutes, 30 minutes and 1 hour.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

As was noted above, the *Bacillus*-based component and/or a feedstuff comprising the same may be used in any suitable form. It may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions may be mixed with feed or administered in the drinking water.

A *Bacillus*-based component, comprising admixing a *Bacillus*-based component as described herein with a feed acceptable carrier, diluent or excipient, and (optionally) packaging.

The feedstuff and/or *Bacillus*-based component may be combined with at least one mineral and/or at least one vitamin. The compositions thus derived may be referred to herein as a premix. The feedstuff may comprise at least 0.0001% by weight of *Bacillus*-based component. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the *Bacillus*-based component.

Preferably, a food or *Bacillus*-based component may further comprise at least one physiologically acceptable carrier. The physiologically acceptable carrier is preferably selected from at least one of maltodextrin, limestone (calcium carbonate), cyclodextrin, wheat or a wheat component, sucrose, starch, $Na_2SO_4$, Talc, PVA and mixtures thereof. In a further embodiment, the food or feed may further comprise a metal ion chelator. The metal ion chelator may be selected from EDTA or citric acid.

In one embodiment a *Bacillus*-based component as described herein (whether or not encapsulated) can be formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbate, glycerol, sucrose, propylene glycol, 1,3-propane diol, glucose, parabens, sodium chloride, citrate, acetate, phosphate, calcium, metabisulfite, formate and mixtures thereof.

In some embodiments, a *Bacillus*-based component as described herein, will be in a physiologically acceptable carrier. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates. Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, capsules, liquids, gels, syrups, slurries and suspensions, for ingestion by the patient. Once formulated, the can be administered directly to the subject. The subjects to be treated can be animals.

It is believed that the composition disclosed herein can produce one or more performance benefits in the animal (i.e., animal performance), the performance benefit being selected from the group consisting of increased bodyweight gain, gain feed ratio, improved gut barrier integrity, decreased mortality, and reduced *E. coli* shedding in feces.

Preferably, "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved gut barrier integrity and/or decreased mortality and/or reduced *E. coli* shedding in feces in comparison to feed or a feed additive composition which does not comprise the composition disclosed herein.

Preferably, by "improved animal performance" it is meant that there is increased feed efficiency and/or increased weight gain and/or reduced feed conversion ratio. As used herein, the term "feed efficiency" refers to the amount of weight gain in an animal that occurs when the animal is fed ad-libitum or a specified amount of food during a period of time.

By "increased feed efficiency" it is meant that the use of a feed additive composition according the present invention in feed results in an increased weight gain per unit of feed intake compared with an animal fed without said feed additive composition being present.

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise a feed additive composition as disclosed herein.

Gut integrity and microbiota appear to be helpful in maintaining gut health. Supporting the intestinal barrier helps to decrease the risk of infection and inflammation. For example, tight junctions are closely associated areas of two cells whose membranes join together forming a barrier virtually impermeable to fluid. The ability to protect tight junction integrity can improve the health of an animal. Tight junctions also need to be maintained to avoid a "leaking gut" which can result in further cell damage. Thus, improving gut integrity by helping or increasing the ability of animal to maintain a well-regulated barrier function that hinder bacteria from entering the animal's body unintentionally is desirable.

Tight junctions, also known as occluding junctions are the closely associated areas of two cells whose membranes join together forming a barrier virtually impermeable to fluid. In the context of gut health, tight junctions are the channels between the gut epithelial cells that can lead to either good or poor gut integrity. When good gut integrity is present, tight junction proteins such as Claudin 3 and Occludin are expressed between two epithelial cells at higher levels, helping to provide a barrier that can prevent the translocation of pathogens from the gut lumen into the systemic circulation (reduced permeability). Claudins are the most important family of tight junction proteins and claudin 3 is one of the genes that encodes for these tight junction proteins. Occludin is another important tight junction protein. Claudins and Occludin were the first tight junctional integral membrane proteins identified. Measurement of tight junction protein RNA can serve as an indicator of barrier integrity and gut health because if tight junctions are not maintained in the gastrointestinal tract of an animal, it can result in permeability that may allow the translocation of pathogens and toxins from the gut lumen into the systemic circulation and, thus compromise animal health or even result in death of the animal (for example sepsis).

Reduced *E. coli* shedding in feces by using the composition as taught herein can reduce further spreading of an *E. coli*-based infection, and improve animal performance as well.

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

In some embodiments, the compositions described herein can improve the digestibility or utilization of dietary hemicellulose or fibre in a subject.

The term survival as used herein means the number of subjects remaining alive. The term "improved survival" may be another way of saying "reduced mortality".

An "increased weight gain" refers to an animal having increased body weight on being fed feed comprising a feed additive composition compared with an animal being fed a feed without said feed additive composition being present.

Non-limiting examples of compositions and methods disclosed herein include:

1. A composition for preventing and/or treating an *E. coli*-based infection in an animal wherein said composition a *Bacillus*-based direct-fed microbial component comprising *Bacillus* strain 3BP5 (NRRL B-50510); *B. amyloliquefaciens* strains 918 (NRRL B-50508), and *Bacillus subtilis* subsp. *subtilis* 15A-P4 (PTA-6507) either alone or in combination with a culture supernatant derived from these strains.
2. The composition of embodiment 1 wherein the said composition produces one or more performance benefits selected from the group consisting of increased bodyweight gain, gain feed ratio, improved gut barrier integrity, decreased mortality and reduced *E. coli* shedding in feces.
3. The composition of embodiments 1 or 2 wherein the direct-fed microbial is in the form of an endospore.
4. The composition of embodiments 1 or 2 wherein said composition further comprises at last one enzyme which, optionally, may be encapsulated.
5. The composition of embodiment 3 wherein said composition further comprises at last one enzyme which, optionally, may be encapsulated.
6. The composition of embodiment 4 wherein the at least one enzyme is selected from the group consisting of phytase, protease, amylase, xylanase and beta-glucanase.
7. The composition of embodiments 1, 2, 5 or 6 wherein said composition is a feed additive composition or a premix.

8. The composition of embodiment 3 wherein said composition is a feed additive composition or a premix.
9. The composition of embodiment 4 wherein said composition is a feed additive composition or a premix.
10. Feed comprising the feed additive composition of embodiment 7.
11. Feed comprising the feed additive composition of embodiments 8 or 9.
12. A kit comprising the feed additive composition of embodiment 7 and instructions for administration.
13. A kit comprising the feed additive composition of embodiments 8 or 9 and instructions for administration.
14. A method for preventing and/or treating an E. coli-based infection in an animal which comprises administering an effective amount of a composition comprising a Bacillus-based direct-fed microbial component comprising Bacillus subtilis strain 3BP5 (NRRL B-50510); Bacillus amyloliquefaciens strains 918 (NRRL B-50508), and Bacillus subtilis subsp. subtilis 15A-P4 (PTA-6507).
15. The method of embodiment 14 wherein the composition produces one or more performance benefits selected from the group consisting of increased bodyweight gain, gain feed ratio, improved gut barrier integrity and reduced E. coli shedding in feces.
16. The method of embodiments 14 or 15 wherein the direct-fed microbial is in the form of an endospore.
17. The method of embodiments 14 or 15 wherein said composition further comprises at last one enzyme which, optionally, may be encapsulated.
18. The method of embodiment 16 wherein said composition further comprises at last one enzyme which, optionally, may be encapsulated.
19. The method of embodiment 17 wherein the at least one enzyme is selected from the group consisting of phytase, protease, amylase, xylanase and beta-glucanase.
20. The method of embodiment 18 wherein the at least one enzyme is selected from the group consisting of phytase, protease, amylase, xylanase and beta-glucanase.
21. The method of embodiments 14, 15, 19 and 20 wherein said composition is a feed additive composition or a premix.
22. The method of embodiment 16 wherein said composition is a feed additive composition or a premix.

EXAMPLE

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY*, 2D ED., John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

Effects of a three-strain *Bacillus* based direct-fed microbial (*Bacillus* strains 3BP5, 918, 15A-P4) on the growth performance, faecal *E. coli* shedding scores and intestinal barrier function of weaned pigs challenged with F18 enterotoxigenic *Escherichia coli*

Materials and Methods

Housing and Environment

The use of animals and experimental protocol is approved by the Animal Experiment Committee. The basal diet, as fed, is formulated to be balanced for energy and protein, and to meet or exceed the nutrient requirements for growing pigs of this age (Table 1) as recommended by the NRC (2012).

The basal diet is divided into portions which are then treated with the direct fed microbials (DFMs) as identified in Table 1. During feed mixing, the mixer is flushed to prevent cross contamination of the diets. Samples are collected from each treatment diet from the beginning, middle, and end of each batch and blended together to DFM counts in feed. Samples from each treatment diet are collected during mixing and stored at −20° C. until required.

TABLE 1

Examples of basal diet composition for pigs in mash form (%, as-fed)

| Item | Basal diet |
| --- | --- |
| Ingredient, % | |
| Corn | 58.07 |
| Soybean meal | 15.00 |
| Whey powder | 9.00 |
| HP300 | 8.50 |
| Fishmeal | 4.00 |
| Soybean oil | 2.00 |
| Limestone | 1.27 |
| Monocalcium phosphate | 0.10 |
| Salt | 0.68 |
| Vitamin premix | 0.20 |
| Trace mineral premix | 0.20 |
| L-Lysine HCL | 0.52 |
| DL-Methionine | 0.19 |
| L-Threonine | 0.16 |
| L-Valine | 0.06 |
| L-Tryptophan | 0.03 |
| Phytase, FTU/kg[2] | 2000 |
| DFM1 | — |
| DFM2 | — |
| Calculated composition | |
| DE, kcal/kg | 3200 |
| ME, kcal/kg | 3407 |
| NE, kcal/kg | 2559 |
| Crude protein, % | 20.34 |
| Ether extract, % | 4.92 |
| Sodium, % | 0.38 |
| Calcium, % | 0.85 |
| SID[3] Lysine, % | 1.40 |
| Total phosphorus, % | 0.53 |
| STTD[4] phosphorus, % | 0.43 |
| SID AA:Lys ratio | |
| Met | 0.36 |
| Met + Cys | 0.55 |
| Thr | 0.59 |

TABLE 1-continued

Examples of basal diet composition
for pigs in mash form (%, as-fed)

| Item | Basal diet |
|---|---|
| Trp | 0.17 |
| Val | 0.64 |

[1] Dietary treatments delivered in mash form in one phase
[2] FTU—phytase units
[3] SID—standardized ileal digestible
[4] STTD—standardized total tract digestible

TABLE 2

Experimental diets identification

| Treatment | Description | DFM, colony forming units/g of feed |
|---|---|---|
| 1 | Control, basal (PC) | N/A |
| 2 | PC challenged with ETEC (NC) | N/A |
| 3 | NC + DFM1[1] | 7.35 × 10$^5$ |
| 4 | NC + DFM2[2] | 1.5 × 10$^5$ |

[1] 2 strains of *Bacillus*: *Bacillus* strains B22 and 15AP4
[2] 3 strains of *Bacillus*: *Bacillus* strains 3BP5, 918 and 15AP4

Experimental Design

A total of 72 newly weaned, mixed sex (50% each of barrows and gilts) piglets weighing 6.44±0.64 kg are used in the 17-day experiment. Each piglet is genetically tested to ensure susceptibility to F18 *E. coli*. The pigs are individually weighed, blocked by weight and randomly assigned within block to 1 of 4 dietary treatments. The pigs are housed with two pigs per pen, and kept in 1 of 2 separate rooms based on their challenge status; 1 smaller room for the 18 non-challenged control pigs (9 pens; PC treatment), and the other bigger room for the 54 challenged pigs (27 pens; 9 pens per treatment for NC, NC+DFM1 and NC+DFM2). All pigs are housed in an environmentally-controlled room. Each pen is equipped with a one-sided, stainless steel self-feeder and a nipple drinker that pigs are allowed access to feed and water ad libitum. The experiment was run over 17 days. It consisted of a 7-day adaptation period to the diets, followed by a 10-day challenge period. Pigs in the NC, NC+DFM1 and NC+DFM2 treatment groups are orally infected with F18 enterotoxigenic *E. coli* (ETEC) on day 7 post weaning (day 7 of the study). The PC treatment group is not challenged with *E. coli*.

Growth Performance and Fecal Sample Collection and Analysis

Body weight and feed consumption is measured at day 0, 7 and 17 (trial end) to monitor average daily gain (ADG), average daily feed intake (ADFI) and gain to feed ratio (G:F). Faecal swabs are collected on day 7 (immediately before challenge) and days post infection (dpi) 1, 2, 3, 4, 5, 6 7, and 10 to asses *E. coli* shedding. Faecal score is visually ranked on a daily basis in a blinded fashion using the following scale: 1=solid; 2=semi-solid; 3=semi-liquid; 4=liquid.

On dpi 10 (last day of the study) one pig from each pen is euthanised by captive bolt followed by exsanguination to collect the following tissues: fresh and fixed ileum and colon segments and ileal and colonic digesta. Ileal tissues segments are analysed by PCR to determine the RNA expression of tight junction proteins that affect tight junction (gut) integrity.

Growth performance data are analyzed using PROC MIXED (SAS 9.4) with initial body weight as a covariate. Time course data are analyzed as repeated measures in PROC GLIMMIX.

Results

Growth performance: During the 7-day adaption period, there is no significant difference in ADG, ADFI or G:F among the four treatments (P>0.10). However, the body-weight gain with NC+DFM2 is numerically greater than all the other treatments. Pigs on the NC+DFM2 diet gained 0.781 kg (final weight−initial weight) during the first 7 days of the study whilst the PC, NC and NC+DFM1 gained 0.239, 0.188 and 0.365 kg, respectively (Table 3).

This means that pigs fed the NC+DFM2 diet also have numerically higher ADG and G:F than all other treatments in the first 7 days of dietary adaptation (Table 3).

TABLE 3

Least square means for effects of dietary treatment on pig growth performance during 1-week adaptation (d 0-7 of study)

| Item | PC | NC | DFM1 | DFM2 | SEM | P-value |
|---|---|---|---|---|---|---|
| Initial Weight | 6.487$^a$ | 6.485$^a$ | 6.469$^a$ | 6.303$^b$ | 0.216 | 0.043 |
| Final Weight | 6.726 | 6.673 | 6.834 | 7.084 | 0.125 | 0.110 |
| ADG, kg | 0.041 | 0.033 | 0.056 | 0.092 | 0.018 | 0.110 |
| ADFI, kg | 0.083 | 0.086 | 0.082 | 0.108 | 0.013 | 0.449 |
| G:F | 0.445 | 0.107 | 0.393 | 0.801 | 0.232 | 0.172 |

After the 10-day challenge period (d 8-17 of the study) the pigs on the NC, NC+DFM1, and NC+DFM2 treatments have a lower final BW (P=0.002), lower ADG (P<0.0001) and lower ADFI (P=0.002) compared to the PC (Table 4). This is an expected outcome of the successful *E. coli* challenge. However, only the NC and NC+DFM1 treatment groups have a lower G:F than the control.

The NC+DFM2 pigs have an intermediate G:F which is 19% higher than the NC (0.647 vs. 0.542) and statistically similar to the PC (Table 4).

Pigs fed the DFM2 gained 2.477 kg during the 10-day challenge period, yet pigs fed the NC or NC+DFM1 gained only 2.312 and 1.881 kg, respectively (Table 4).

TABLE 4

Least square means for effects of dietary treatment on pig growth performance during the 10-day challenge period (d 8-17 of study)

| Item | PC | NC | NC + DFM1 | NC + DFM2 | SEM | P-value |
|---|---|---|---|---|---|---|
| Initial Weight | 6.726 | 6.673 | 6.834 | 7.084 | 0.125 | 0.110 |
| Final Weight | 10.578$^a$ | 8.985$^b$ | 8.715$^b$ | 9.561$^b$ | 0.382 | 0.002 |
| ADG, kg | 0.386$^a$ | 0.181$^b$ | 0.152$^b$ | 0.229$^b$ | 0.036 | <.0001 |
| ADFI, kg | 0.470$^a$ | 0.348$^b$ | 0.294$^b$ | 0.348$^b$ | 0.033 | 0.002 |
| G:F | 0.817$^a$ | 0.542$^b$ | 0.506$^b$ | 0.647$^{ab}$ | 0.091 | 0.040 |

*E. coli* shedding scores: Overall the PC treatment *E. coli* shedding score (SS) is lower than the challenged treatments, as expected (P<0.0.01, Table 6). The NC+DFM2 treatment increases SS on 2 dpi (P=0.04) but decreases SS on 7 dpi (P=0.003) compared to NC (Table 5). The NC+DFM2 numerically reduced SS vs. the NC on dpi 5 and 10 (Table 5).

Overall, NC+DFM1 and NC+DFM2 numerically reduce *E. coli* faecal shedding compared to the NC (1.96 and 2.03, respectively, vs. 2.12; Table 6).

TABLE 5

Effect of dietary treatment on ETEC shedding[1] during each day post infection

| | Treatment | | | | Contrast[2] | | |
|---|---|---|---|---|---|---|---|
| DPI | PC | NC | NC + DFM1 | NC + DFM2 | SEM | 1 | 2 | 3 |
| 0 | 0.00 | 0.00 | 0.00 | 0.00 | 0.000 | 1.000 | 1.000 | 1.000 |
| 1 | 0.00 | 2.31 | 1.69 | 2.14 | 0.107 | <.0001 | 0.039 | 0.577 |
| 2 | 0.00 | 2.46 | 2.50 | 3.08 | 0.108 | <.0001 | 0.900 | 0.043 |
| 3 | 0.00 | 2.76 | 3.00 | 3.17 | 0.098 | <.0001 | 0.430 | 0.182 |
| 5 | 0.00 | 3.09 | 2.63 | 2.99 | 0.112 | <.0001 | 0.159 | 0.766 |
| 7 | 0.00 | 3.24 | 2.71 | 2.25 | 0.115 | <.0001 | 0.109 | 0.003 |
| 10 | 0.00 | 1.07 | 1.17 | 0.71 | 0.116 | 0.001 | 0.760 | 0.293 |

[1]ETEC shedding score system: 0 = negative, 1 = growth in section 1, 2 = growth in section 2, 3 = growth in section 3, 4 = growth in section 4
[2]Contrasts: 1) PC vs NC, 2) NC vs NC + DFM1, 3) NC vs NC + DFM2

TABLE 6

Effect of dietary treatment on ETEC shedding for the overall 10-day challenge period

| Contrast | LS Means | P-value |
|---|---|---|
| PC vs. NC | 0 vs. 2.12 | <.0001 |
| PC vs. All challenged treatments | 0 vs. 3.05 | <.0001 |
| NC vs. NC + DFM1 | 2.12 vs. 1.96 | 0.380 |
| NC vs. NC + DFM2 | 2.12 vs. 2.03 | 0.638 |

Fecal scores: From day 3 post infection to 8 dpi the PC has lower fecal scores (FS) than the NC, as expected (P<0.0001, Table 7). At 2 dpi pigs fed NC+DFM2 have higher FS than NC pigs; however, on dpi 7 DFM 2 pigs have lower FS than NC pigs (P<0.10; Table 7).

Also, on dpi 4-10 pigs fed DFM2 have numerically lower FS than NC fed pigs. DFM1 did not significantly reduce FS vs. the NC on any dpi (Table 7).

TABLE 7

Effect of dietary treatment on fecal score[1] during each day post infection

| | Treatment | | | | | Contrast[2] | | |
|---|---|---|---|---|---|---|---|---|
| DPI | PC | NC | DFM1 | DFM2 | SEM | 1 | 2 | 3 |
| 0 | 1.90 | 0.35 | 0.63 | 0.63 | 0.121 | <.0001 | 0.421 | 0.421 |
| 1 | 1.35 | 1.25 | 0.75 | 1.50 | 0.121 | 0.756 | 0.144 | 0.465 |
| 2 | 1.15 | 1.15 | 1.31 | 1.88 | 0.121 | 1.000 | 0.635 | 0.035 |
| 3 | 0.30 | 1.85 | 2.45 | 2.06 | 0.123 | <.0001 | 0.089 | 0.534 |
| 4 | 0.45 | 2.27 | 2.00 | 2.13 | 0.122 | <.0001 | 0.432 | 0.670 |
| 5 | 0.00 | 2.35 | 2.19 | 2.19 | 0.121 | <.0001 | 0.635 | 0.635 |
| 6 | 0.00 | 2.25 | 2.19 | 2.19 | 0.121 | <.0001 | 0.855 | 0.855 |
| 7 | 0.10 | 1.92 | 2.56 | 1.31 | 0.124 | <.0001 | 0.065 | 0.090 |
| 8 | 0.10 | 1.58 | 2.19 | 1.24 | 0.124 | <.0001 | 0.084 | 0.333 |
| 9 | 0.15 | 0.53 | 1.13 | 0.52 | 0.124 | 0.251 | 0.088 | 0.985 |
| 10 | 0.25 | 0.70 | 0.63 | 0.66 | 0.124 | 0.177 | 0.841 | 0.932 |

[1]Fecal score system: 0 = normal, 1 = semi-solid, 2 = mild diarrhea 3 = severe diarrhea
[2]Contrasts: 1) PC vs NC, 2) NC vs DFM1, 3) NC vs DFM2

Tight Junction Protein RNA Expression (Gut Integrity):

Tight junctions, also known as occluding junctions, are the closely associated areas of two cells whose membranes join together forming a barrier virtually impermeable to fluid. In the context of gut health, tight junctions are the channels between the gut epithelial cells that can lead to either good or poor gut integrity. When good gut integrity is present, tight junction proteins such as Claudin 3 and Occludin are expressed between two epithelial cells, helping to provide a barrier that can prevent the translocation of pathogens from the gut lumen into the systemic circulation. Claudins are the most important family of tight junction proteins and claudin 3 is one of the genes that encodes for these tight junction proteins. Occludin is another important tight junction protein. Claudins and Occludin were the first tight junctional integral membrane proteins identified. Measurement of tight junction protein RNA can serve as an indicator of barrier integrity and gut health because if tight junctions are not maintained in the gastrointestinal tract of an animal, it can result in permeability that may allow the translocation of pathogens and toxins from the gut lumen into the systemic circulation and, thus comprise animal health or even result in death of the animal.

It was found in the experiment that dietary treatments have no significant effect on the RNA expression of tight junction protein Claudin 3; however, the PC is numerically higher than the NC and NC+DFM1 (0.982 vs. 0.638 and 0.648, respectively; FIG. 1). However, the NC+DFM2 shows RNA expression of Claudin 3 that is numerically similar to the PC (0.945 vs. 0.982; FIG. 1).

Treatment, i.e., DFM1 or DFM2, has a significant effect on RNA expression of tight junction protein Occludin, whereby the NC and NC+DFM1 have lower Occludin expression than the PC, but NC+DFM2 is intermediate between the PC and the NC (P=0.045). The P-value shows overall differences between the treatments as shown in FIG. 1.

What is claimed:

1. A method for treating an enterotoxigenic *E. coli* (ETEC)-based infection in swine which comprises orally administering an effective amount of a composition comprising a *Bacillus*-based direct-fed microbial component comprising *Bacillus* strains 3BP5 (NRRL B-50510), 918 (NRRL B-50508), and 15-AP4 (PTA-6507) to the swine.

2. The method of claim 1 wherein the composition produces one or more performance benefits selected from the group consisting of increased bodyweight gain, gain feed ratio, improved gut barrier integrity, reduced mortality, and reduced *E. coli* shedding in feces.

3. The method of claim 1 wherein the *Bacillus*-based direct-fed microbial is in the form of an endospore.

4. The method of claim 1 wherein said composition further comprises at least one enzyme which, optionally, may be encapsulated.

5. The method of claim 3 wherein said composition further comprises at least one enzyme which, optionally, may be encapsulated.

6. The method of claim 4 wherein the at least one enzyme is selected from the group consisting of phytase, protease, amylase, xylanase and beta-glucanase.

7. The method of claim 5 wherein the at least one enzyme is selected from the group consisting of phytase, protease, amylase, xylanase and beta-glucanase.

8. The method of claim 1 wherein said composition is a feed additive composition or a premix.

9. The method of claim 3 wherein said composition is a feed additive composition or a premix.

10. The method of claim 4 wherein said composition is a feed additive composition or a premix.

* * * * *